United States Patent
Parris

(10) Patent No.: US 6,249,698 B1
(45) Date of Patent: Jun. 19, 2001

(54) INFARED RADIATION THERAPY DEVICE

(75) Inventor: Danny M. Parris, Inola, OK (US)

(73) Assignee: Therapia LLC, Scottsdale, AZ (US)

( * ) Notice: Subject to any disclaimer, the term of this patent is extended or adjusted under 35 U.S.C. 154(b) by 0 days.

(21) Appl. No.: 09/319,835

(22) PCT Filed: Dec. 11, 1997

(86) PCT No.: PCT/US97/23154

§ 371 Date: Jun. 11, 1999

§ 102(e) Date: Jun. 11, 1999

(87) PCT Pub. No.: WO98/25667

PCT Pub. Date: Jun. 18, 1998

(51) Int. Cl.[7] .................................................. A61N 1/00
(52) U.S. Cl. .................................................. 607/3; 607/88
(58) Field of Search ............................... 607/3, 1, 88, 90, 607/89, 91, 93

(56) References Cited

U.S. PATENT DOCUMENTS 5,304,207 * 4/1994 Stromer ..................................... 607/3
5,620,463 * 4/1997 Drolet ....................................... 607/3

* cited by examiner

*Primary Examiner*—George R. Evanisko
(74) *Attorney, Agent, or Firm*—Schweitzer Cornman Gross & Bondell LLP

(57) ABSTRACT

An apparatus for treatment of a living body includes a frequency generator for generating an electrical output signal in the audio or sub-audio range. A plurality of transducers for applying different treatment modalities to one or more selected locations of the body are driven by the generator. Each of the treatment applicators is capable of being driven at a plurality of operating frequencies. A modulator coupled to the frequency generator and to the applicators generates individual drive signals for each of the applicators and permits individual control over the timing and sequence of their operation. One of the applicators is an infrared radiation diode device.

5 Claims, 1 Drawing Sheet

INFARED RADIATION THERAPY DEVICE

BACKGROUND OF THE INVENTION

The present invention relates to therapy processes to be applied to a human or animal body, and in particular to the use of single or multiple modalities for the application of pulsed energy to the body for therapeutic purposes.

In the present inventor's U.S. Pat. No. 4,646,743 of Mar. 3, 1987, an apparatus is disclosed in which infrared electromagnetic radiation of a selected frequency or frequency range is applied to a body for therapy purposes. The radiation may be produced by a broad band infrared diode array, the drive for which is modulated at a high frequency. The diodes are placed in contact with a selected portion of the body for treatment. The disclosure of the aforementioned U.S. Pat. No. 4,646,743 is incorporated herein by reference.

It has now been found that the modulation of infrared energy at relatively low frequencies, typically in the sonic or sub-sonic range, can provide enhanced therapeutic effects for an IR therapy device. Such effects can be further improved by combining such infrared treatment with the concurrent application of other energy-transmission modalities, such as vibration or electronic stimulation, modulated at the same frequency or at a frequency associated with the frequency of the infrared radiation.

It is accordingly a primary purpose of the present invention to provide an improved device for irradiating the body of a subject to be treated by means of infrared radiation modulated at one or more audio frequencies.

Still a further purpose of the present invention is to provide a therapy device in which such infrared radiation may be combined with one or more additional modalities for the application of resonant energy to the subject.

Still a further purpose of the present invention is to provide a therapy application device which may have a single output applicator capable of applying one or more therapy modalities in conjunction with each other.

Yet another purpose of the present invention is to provide a method for the treatment of tissues by the application of energy modulated at an audio or sub-audio rate, wherein the energy is in the form of infrared energy, either alone or applied concurrently with one or more other energy modes.

BRIEF DESCRIPTION OF THE INVENTION

In accordance with the foregoing and further purposes and objects, the present invention comprises an apparatus having an infrared emitter, the output of which may be modulated at a chosen audio or sub-audio frequency generated by a frequency source to which the emitter is coupled. Additional energy transducers may also be coupled to the frequency source whereby their outputs are similarly modulated at the chosen frequency, or a frequency related to the chosen frequency, such as a multiple or sub-multiple thereof. These transducers may include means for generating electrical or magnetic fields, as well as mechanical energy.

A control system is provided to regulate and adjust the timing and relationships between and among the transducers, and to adjust the modulation frequency or frequencies. This allows a desired therapy regimen to be established, whereby the controlled treatment modalities may be applied sequentially or simultaneously as appropriate.

BRIEF DESCRIPTION OF THE DRAWINGS

A fuller understanding of the present invention will be accomplished upon consideration of the following description of a detailed, but nonetheless illustrative embodiment of the invention, when taken in conjunction with the annexed FIGURE which presents a block diagram of the invention.

DETAILED DESCRIPTION OF THE INVENTION

Figure 1:
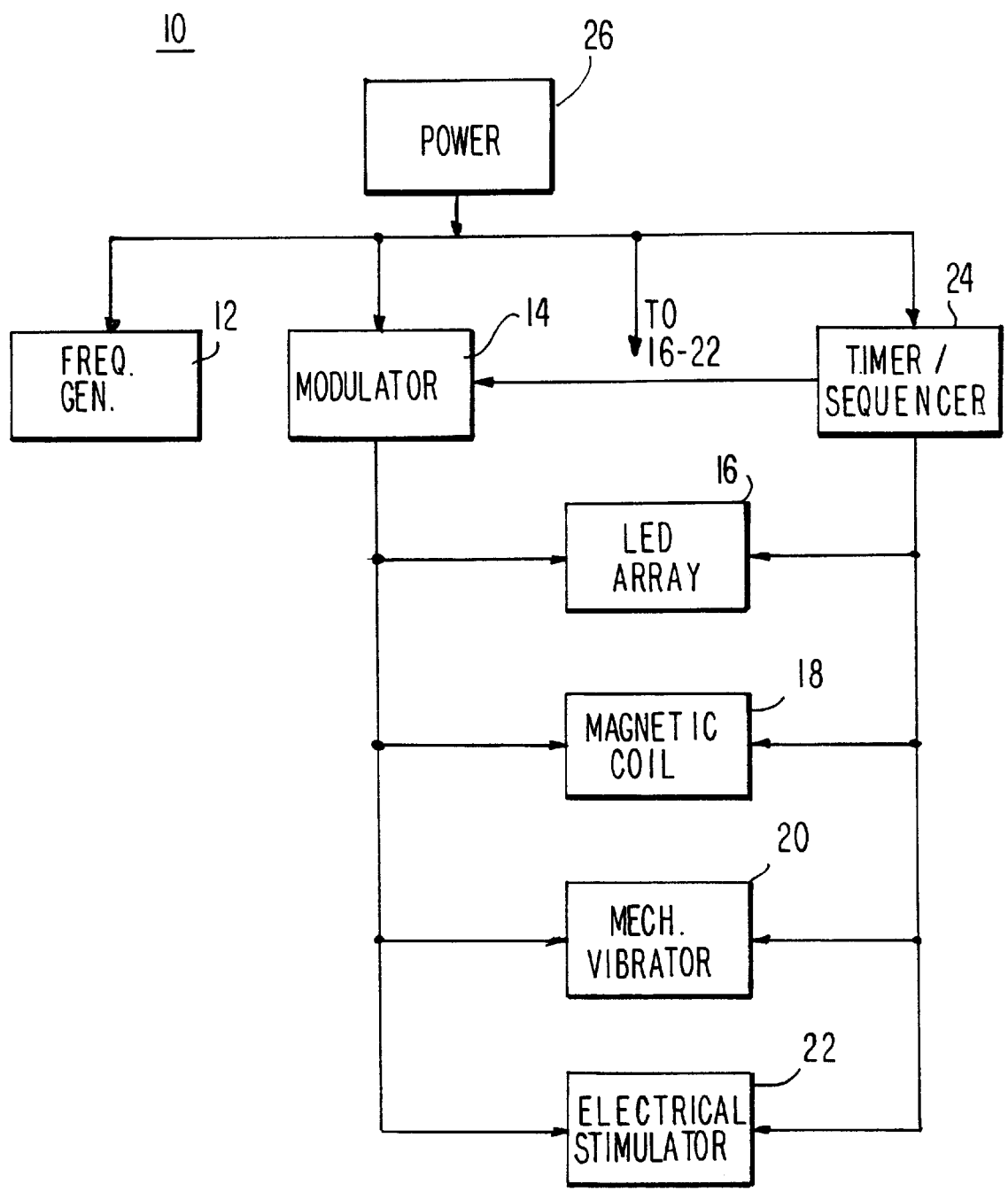

Referring to the FIGURE, an apparatus 10 constructed in accordance with the present invention includes a frequency generator or oscillator 12, particularly adapted to generate an electrical signal output at a chosen frequency in the audio or sub-audio range, which signal drives a modulator 14. The output of the frequency generator is preferably a sinusoid, but may also be a ramp or other waveform. The modulator 14 in turn modulates or controls the application of drive power, and thus the operation of one or more therapy applicator means 16–22, each of which is adapted to apply a particular form of therapy treatment to a subject. Modulator 14 preferably includes divider and multiplier circuitry which allow multiple outputs, at harmonics or sub-harmonics of the output frequency of frequency generator 12 to be simultaneously generated and delivered as desired to the various therapy applicator means.

As depicted in the FIGURE, the applicator means may include a light-emitting diode (LED) array 16. Such applicator is intended to supply infrared and/or near-infrared radiation to the subject as a treatment modality, and may include one or more LEDs arranged as required, such as disclosed in U.S. Pat. No. 4,646,743 in order to apply the infrared radiation to a selected portion of the subject's body. Second applicator means 18 may comprise one or more electromagnetic coils, as known in the art, adapted and arranged to allow a generated magnetic field to be directed at a treatment site. The coils may, for example, be of a construction that allow them to encircle a treatment site, such as a portion of a limb, or otherwise may be of a toroidal or other form to direct a generated magnetic field outwardly towards a treatment site.

A third applicator means 20 may comprise means for providing a mechanical vibration to a treatment site. Such a construction may be, for example, a magnetically-driven reciprocating device coupled to the limb. Fourth applicator 22 may be an electrical stimulator device, as known in the art, adapted to apply an appropriate electrical current to a target site on the body.

Each of the applicators 16–22 are concurrently driven by the modulator 14, whereby the primary form of stimulus applied by the applicator is modulated at the rate of, or at a harmonic or sub-harmonic of the frequency generator 12. For example, the infrared radiation generated by LED array 16 is modulated or switched at the chosen frequency rate. Simultaneously, the magnetic field generated by the electrical current in the coil of the applicator 18 is similarly pulsed, as are the mechanical vibrations from source 20 and the electrical stimulations generated by source 22. Each of these sources may be effectively modulated by modulating the drive electrical power to the respective transducer. It is to be recognized, however, that the precise manner in which each applicator means may be controlled may vary. For example, the magnetic field may be pulsed on and off at the rate set by the frequency generator, or alternatively may be modulated in a continuous manner by the waveform generated by the frequency generator. The term "modulated" as used herein is intended to encompass any such various means of control.

The applicator means or transducer for each of the therapy modes may be combined into a single applicator unit, whereby one or more of the stimulations may be applied to the same treatment location. Alternatively, each of the applicator means may comprise a separate applicator unit, each of which may be placed as necessary with respect to the subject undergoing therapy, allowing multiple sites to be treated individually.

A prime feature of the present invention is the ability to correlate and coordinate the application of the individual therapy modes. This is accomplished through timer sequencer 24, which is coupled both to the applicator means 16–22 and to modulator 14. By the use of appropriate gating circuitry, as known in the art, each of the applicators can be individually enabled on a pulsed or continuous basis. In addition, means may be provided to control the overall therapy timer for each of the applicators. Further, the relationships between and among the operating cycles for the applicators can be programmed. This allows the applicators to be operated simultaneously, sequentially, or in any desired pattern or relationship to each other, with individual control over the modulation frequency the timing and duration of the treatment, as well as the duty cycle of each of the applicators. As this timer/sequencer is preferably coupled to the modulator 14, it may also include means to direct a chosen modulator output to the appropriate applicator. For example, modulation at a first frequency F may be delivered to LED array 16, which magnetic coil 18 is modulated with a first harmonic of frequency 2F. The timer/sequencer 24 may preferably be microprocessor-based, with appropriate indicators associated with each of the applicators to allow a desired therapy protocol to be established. The microprocessor may be further provided with memory means to allow pre-programming of selected treatment modalities.

Frequency generator 12 may further provide for a choice of modulation waveforms, as well as for continuous variation of its output frequency. It has been determined that the following frequencies may be of particular value for modulating the outputs of the present invention. Each of the frequencies set forth herein are in Hz.

0.853; 0.9647; 1.022; 1.147; 1.287; 1.364; 1.5311; 1.718; 1.929; 2.044; 2.294; 2.575; 2.728; 3.062; 3.437; 3.858; 4.087; 4.588; 5.150; 5.456; 6.125; 6.875; 7.717; 8.175; 9.177; 10.30; 10.91; 12.25; 13.75; 15.43; 16.35; 18.35; 20.60; 21.82; 24.50 27.50; 30.87; 32.70; 36.71; 41.20; 43.65; 49.00; 55.00; 61.74; 65.40; 73.42; 82.41; 87.31; 98.00; 110.0; 123.47; 130.80; 146.83; 164.81; 14.61; 196.00; 220.0; 246.60; 261.60; 293.66; 329.63; 349.23; 392.00; 440.0; 493.88; 523.20; 587.33; 659.26; 698.46; 783.99; 880.0; 987.77; 1046.40; 1174.70; 1318.50; 1396.90; 1568.00; 1760; 1975.5; 2092.80; 2349.30; 2637.00; 2793.80; 3136.00; 3520; 3951.10; 4185.60; 4698.60; 5274.00; 5587.60; 6272.00; 7040; 7902.20; 8371.20; 9397.20; 10548.00; 11175.20; 12544.00

These frequencies correspond to the primary frequencies of musical notes and sub-harmonics thereof.

The present invention provides an efficient and means of applying a variety of treatment modalities to a subject in a manner which allows for full coordination and synchronization over the choice of modalities employed. It is to be recognized by those skilled in the art that modifications and adaptations of the present invention can be achieved without departing from the intended scope of the invention.

I claim:

1. A living body treatment apparatus, comprising a frequency generator for generating an electrical output signal in the audio and sub-audio range, a plurality of means for applying different treatment modality outputs to one or more selected locations of the body, each of said means being capable of being driven simultaneously with the other of said means and being capable of being driven at a plurality of operating frequencies, said plurality of means including an infrared radiation diode applicator; modulator means coupled to an output of said frequency generator and to each of said plurality of treatment modality application means for generating drive signals for each of said application means at an individual chosen frequency; and means coupled to said plurality of treatment modality application means for individually controlling the timing and sequence of the simultaneous operation thereof.

2. The apparatus of claim 1, wherein said modulator means includes means for generating a plurality of simultaneous drive signals.

3. The apparatus of claim 2, wherein said means for generating a plurality of drive signals comprises means for generating drive signals at chosen harmonics and sub-harmonics of the frequency of the output signal of said frequency generator.

4. The apparatus of claim 1, wherein said plurality of treatment modality applicators further includes at least one applicator chosen from the group consisting of magnetic field generators, mechanical vibrators and electric stimulators.

5. The apparatus of claim 1, wherein said frequency generator is a frequency generator for generating frequencies in the range of 0.853 to 12544 Hz corresponding to the primary frequencies of musical notes and sub-harmonics thereof.

* * * * *